(12) United States Patent
Vijay

(10) Patent No.: US 8,007,428 B2
(45) Date of Patent: *Aug. 30, 2011

(54) CARDIAC VENTRICULAR GEOMETRY RESTORATION DEVICE AND TREATMENT FOR HEART FAILURE

(76) Inventor: Venkataramana Vijay, Staten Island, NY (US)

( * ) Notice: Subject to any disclaimer, the term of this patent is extended or adjusted under 35 U.S.C. 154(b) by 552 days.

This patent is subject to a terminal disclaimer.

(21) Appl. No.: 12/017,804

(22) Filed: Jan. 22, 2008

(65) Prior Publication Data

US 2008/0177130 A1    Jul. 24, 2008

Related U.S. Application Data

(63) Continuation of application No. 11/457,648, filed on Jul. 14, 2006, now Pat. No. 7,320,665, which is a continuation-in-part of application No. 11/070,789, filed on Mar. 2, 2005, now abandoned.

(51) Int. Cl.
  *A61M 25/10* (2006.01)
(52) U.S. Cl. ............ 600/16; 600/17; 604/912; 604/913; 604/915; 604/916
(58) Field of Classification Search .......... 604/912–913, 604/915–916, 96.01, 103, 103.09, 920–921; 600/16–18

See application file for complete search history.

(56) References Cited

U.S. PATENT DOCUMENTS

| | | | |
|---|---|---|---|
| 3,577,992 A * | 5/1971 | Merry et al. ............ 604/99.02 |
| 4,861,330 A | 8/1989 | Voss | |
| 5,129,394 A | 7/1992 | Mehra | |
| 5,409,444 A | 4/1995 | Kensey et al. | |
| 5,571,161 A | 11/1996 | Starksen | |
| 5,961,440 A | 10/1999 | Schweich, Jr. et al. | |
| 5,971,910 A | 10/1999 | Tsitlik et al. | |
| 6,024,096 A | 2/2000 | Buckberg | |
| 6,045,497 A | 4/2000 | Schweich, Jr. et al. | |
| 6,050,936 A | 4/2000 | Schweich, Jr. et al. | |
| 6,063,082 A | 5/2000 | DeVore et al. | |
| 6,077,214 A | 6/2000 | Mortier et al. | |
| 6,125,852 A | 10/2000 | Stevens et al. | |
| 6,126,590 A | 10/2000 | Stevens et al. | |
| 6,156,254 A * | 12/2000 | Andrews et al. ............ 264/231 |

(Continued)

FOREIGN PATENT DOCUMENTS

WO   WO 03/061455 A2   7/2003

OTHER PUBLICATIONS

Walker, Joseph C. et al. "Helical Myofiber Orientation after Myocardial Infarction and Left Ventricular Surgical Restoration in Sheep" Thoracic and Cardiovascular Surgery (1).

(Continued)

*Primary Examiner* — Carl H Layno
*Assistant Examiner* — Jessica Sarcione
(74) *Attorney, Agent, or Firm* — Gordon & Jacobson, PC

(57) ABSTRACT

Methods for cardiac ventricular restoration include delivering an implantable expandable device into the ventricle via a catheter. The expandable device is anchored either to the wall of the left ventricle or to the inter-ventricular septum and then expanded. When expanded, the device assumes a size and shape which fills the lower portion of the ventricular cavity restoring the normal volume and ellipsoid shape of the remaining portion of the cavity and favorably altering myocardial oxygen demand and wall stress.

18 Claims, 20 Drawing Sheets

U.S. PATENT DOCUMENTS

| | | |
|---|---|---|
| 6,206,820 B1 | 3/2001 | Kazi et al. |
| 6,221,104 B1 | 4/2001 | Buckberg et al. |
| 6,251,093 B1 | 6/2001 | Valley et al. |
| 6,350,248 B1 | 2/2002 | Knudson et al. |
| 6,406,420 B1 | 6/2002 | McCarthy et al. |
| 6,423,031 B1 | 7/2002 | Donlon |
| 6,439,237 B1 | 8/2002 | Buckberg et al. |
| 6,450,171 B1 | 9/2002 | Buckberg et al. |
| 6,537,198 B1 | 3/2003 | Vidlund et al. |
| 6,544,167 B2 | 4/2003 | Buckberg et al. |
| 6,629,921 B1 | 10/2003 | Schweich, Jr. et al. |
| 6,651,672 B2 | 11/2003 | Roth |
| 6,681,773 B2 | 1/2004 | Murphy et al. |
| 6,702,763 B2 | 3/2004 | Murphy et al. |
| 6,852,076 B2 | 2/2005 | Nikolic et al. |
| 6,994,093 B2 | 2/2006 | Murphy et al. |
| 2001/0041821 A1 | 11/2001 | Wilk |
| 2002/0022860 A1 | 2/2002 | Borillo et al. |
| 2002/0029783 A1 | 3/2002 | Stevens et al. |
| 2002/0133054 A1 | 9/2002 | Murphy et al. |
| 2002/0133143 A1 | 9/2002 | Murphy et al. |
| 2002/0133182 A1 | 9/2002 | Murphy et al. |
| 2002/0133227 A1 | 9/2002 | Murphy et al. |
| 2002/0165425 A1 | 11/2002 | Yoon et al. |
| 2003/0045896 A1 | 3/2003 | Murphy et al. |
| 2003/0050659 A1 | 3/2003 | Murphy et al. |
| 2003/0109770 A1 | 6/2003 | Sharkey et al. |
| 2003/0181940 A1 | 9/2003 | Murphy et al. |
| 2003/0187362 A1 | 10/2003 | Murphy et al. |
| 2003/0192561 A1 | 10/2003 | Murphy et al. |
| 2005/0015109 A1 | 1/2005 | Lichtenstein |
| 2005/0075723 A1 | 4/2005 | Schroeder et al. |
| 2005/0154252 A1 | 7/2005 | Sharkey et al. |
| 2006/0106403 A1 | 5/2006 | Schaller |

OTHER PUBLICATIONS

A Guide to Surgical Ventricular Restoration for the Referring Physician. Chase Medical. Richardson, Texas. (32 pages).

Kern, Morton J. The Cardiac Catheterization Handbook. St. Louis, MO: Mosby—Year Book, Inc., 1991. (15 pages).

Moses, H. Weston et al. A Practical Guide to Cardiac Pacing, Fourth Edition. 1995. (5 pages).

"Theory of Operation," "CSD Specifications," etc. Acorn Cardiovascular, Inc., 2000. Brochures. (9 pages).

Sharkey, Hugh et al. Left Ventricular Apex Occluder, Description of a Ventricular Partitioning Device, www.europcronline.com.

* cited by examiner

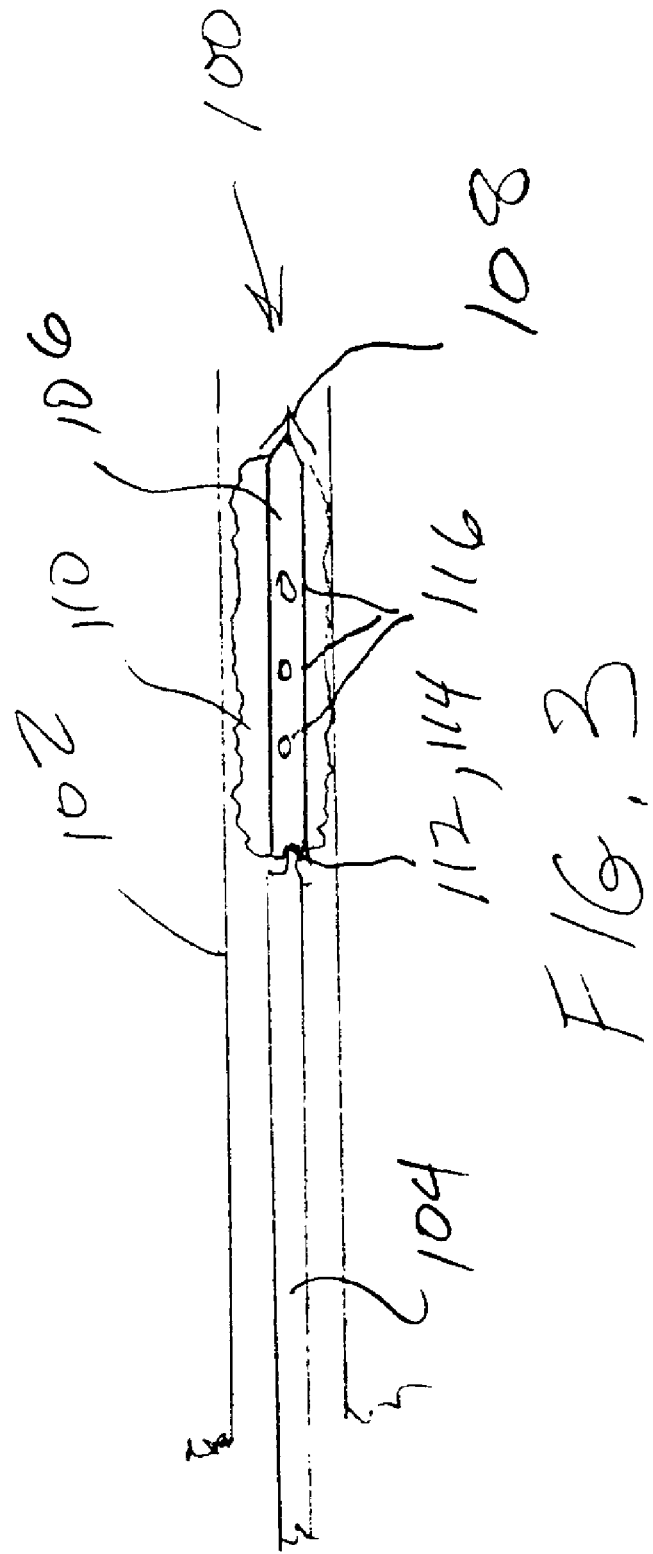

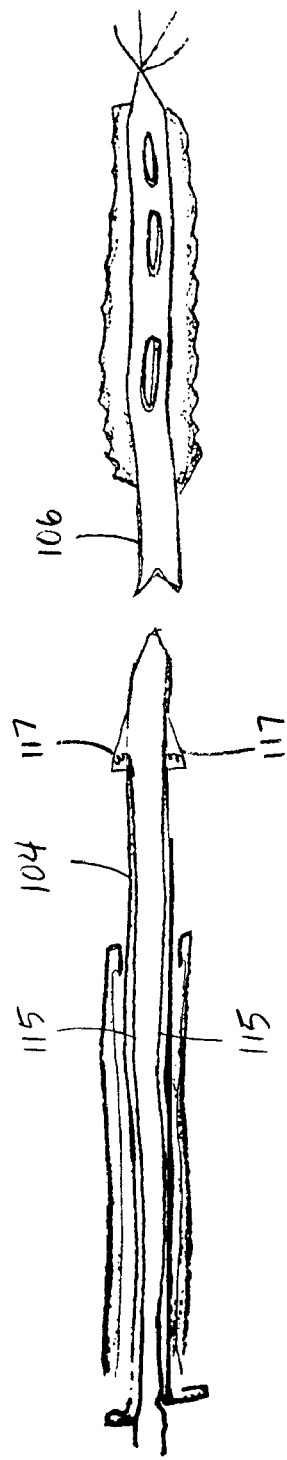
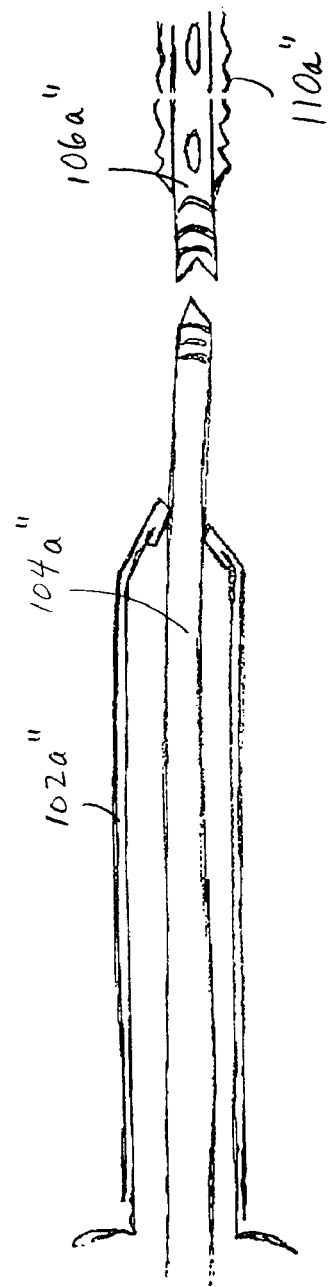
FIG. 3A
FIG. 8A

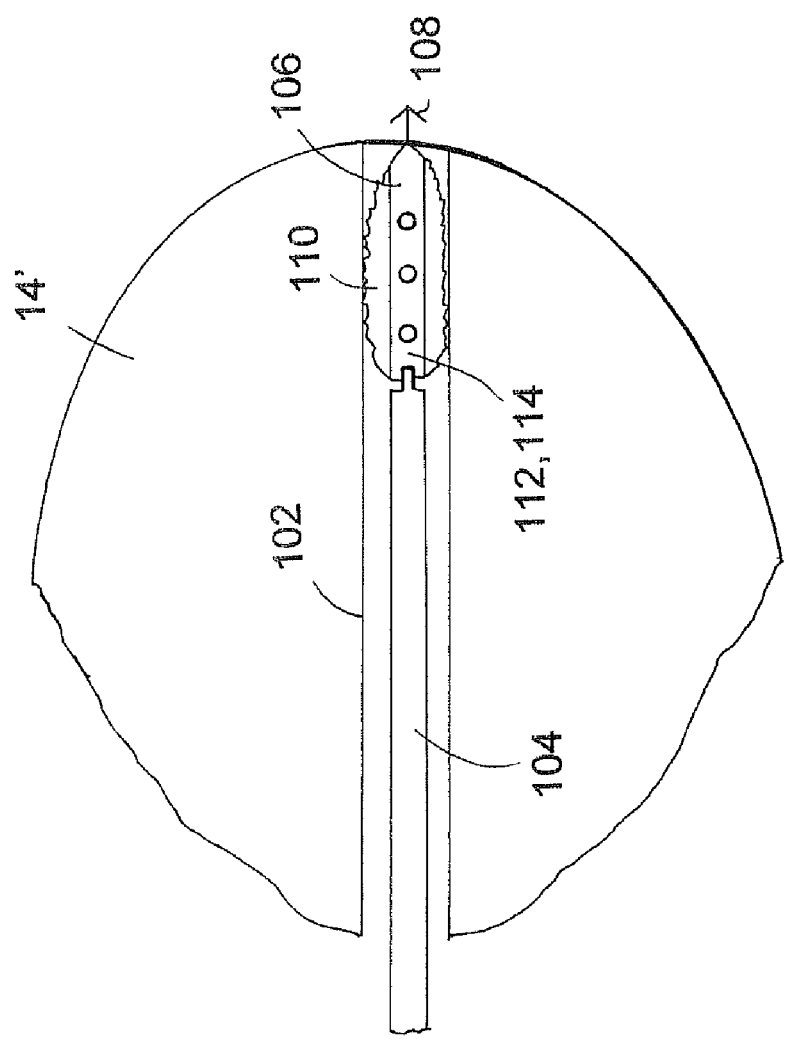

CARDIAC VENTRICULAR GEOMETRY RESTORATION DEVICE AND TREATMENT FOR HEART FAILURE

CROSS-REFERENCE TO RELATED APPLICATIONS

This application is a continuation of U.S. Ser. No. 11/457,648, filed Jul. 14, 2006, to be issued as U.S. Pat. No. 7,320,665, which is a continuation-in-part of U.S. Ser. No. 11/070,789, filed Mar. 2, 2005, now abandoned, which are hereby incorporated by reference herein in their entireties.

BACKGROUND OF THE INVENTION

1. Field of the Invention

This invention relates broadly to methods and apparatus for performing a heart reshaping intervention. More particularly, this invention relates to methods and apparatus for minimally invasive restoration of the left ventricle in patients suffering from congestive heart failure.

2. State of the Art

In the U.S., approximately 5 million patients are currently diagnosed with congestive heart failure (CHF). CHF generally relates to a dysfunction of the left ventricle. About one third of the patients suffering from CHF have a form of CHF which results from a myocardial infarction (MI). The MI progressively increases the residual volume of blood in the left ventricle, due to stagnation from decreasing contractility of the heart muscle.

The increase in blood volume also results in an increase in left ventricular pressure which increases stress on the wall of the left ventricle. The stress requires the myocardium to work harder which increases oxygen demand. Since oxygen delivery to the heart has already been reduced because of coronary artery disease, the MI and the resulting reduced ventricular output, heart muscle tissue dies and the ventricle expands. This causes the myocardium to stretch, thin out and distend, further decreasing heart performance, decreasing the thickness of the ventricle wall and increasing wall stress.

FIG. 1 shows a normal heart 10 having right ventricle 12, left ventricle 14, right atrium 16 and left atrium 18. Though not illustrated, those skilled in the art will appreciate that there are a pair of valves between each ventricle and its associated atrium. The ventricles are separated by an inter-ventricular septum 20. The left ventricle 14 has what is called a generally elliptical (ellipsoidal) shape.

FIG. 2 shows a heart 10' suffering from CHF. The left ventricle 14' is enlarged and assumes a circular (spherical) shape. The stress on the ventricle wall is determined by the Laplace Law as illustrated in Equation 1, below.

$$\text{wall stress} = \frac{(\text{pressure in cavity}) \cdot (\text{radius of cavity})}{2 \cdot (\text{wall thickness})} \quad (1)$$

Thus, as wall thickness is decreased, wall stress increases. This increased wall stress and oxygen demand cause a relative chronic myocardial ischemic state which results in decreased pump function.

It has also been discovered that the change in the shape of the left ventricle adversely affects the way the heart muscle fibers work. The normal ellipsoidal shape most efficiently assists in blood flow through the left ventricle.

State of the art methods for treating CHF involve extremely invasive open heart surgery. For example, use of a "ventricular restoration patch" installed via "purse string" sutures is disclosed in U.S. Pat. No. 6,544,167. The patch seals off a portion of the ventricle thereby reducing the volume and restoring the shape of the cavity. However, installation of the patch requires incision into the left ventricle which severs muscle fibers and the subsequent healing scar increases the risk of arrhythmia.

Another method described in U.S. Pat. No. 6,126,590 involves wrapping the heart in a mesh and suturing the mesh to the heart. The mesh constricts both right and left ventricles, thus not allowing them to fill completely in diastole. It also may cause a constrictive effect on the ventricles known as the tamponade effect.

Yet another method for treating CHF is described in U.S. Pat. No. 6,537,198 and involves the use of trans-ventricular wires anchored by external fixation buttons on either side of the left ventricle. This method puts a compressive force on the ventricle but also results in a mid-level constriction without favorably altering volume, pressure, or wall stress.

Because of the highly invasive nature of these treatments, many CHF patients are not suitable candidates for the surgery.

SUMMARY OF THE INVENTION

It is therefore an object of the invention to provide methods and apparatus for treating CHF.

It is another object of the invention to provide methods and apparatus for reducing the volume of the left ventricle.

It is a further object of the invention to provide methods and apparatus for restoring the left ventricular cavity to an ellipsoidal shape It is also an object of the invention to provide minimally invasive methods and apparatus for achieving the above objects without the side effects of the prior art methods and apparatus.

In accord with these objects, which will be discussed in detail below, the methods of the present invention include delivering an implantable expandable device into the left ventricle via a catheter. The expandable device is anchored either to/through the wall of the left ventricle or to/through the inter-ventricular septum and then expanded. When expanded, the device assumes a size and shape which fills the lower portion of the ventricular cavity thus restoring the volume and ellipsoidal shape of the remaining portion of the cavity. According to one embodiment, the device is a balloon which is expanded by filling it with fluid such as saline. It is anchored with an anchor which extends into or through either the wall of the left ventricle or the inter-ventricular septum. There are two versions of the first embodiment, one having a central stem that extends all the way through the balloon to its opposite end. The other has a very short stem which just extends into the balloon. In both cases the stem includes a valve and an inflation tube coupling. The coupling allows the inflation tube to be coupled to and uncoupled from the balloon and the valve prevents saline from leaking out of the balloon after the tube is uncoupled from it. A second embodiment includes a pair of umbrella-like structures, at least one of which is covered with a biocompatible membrane and is provided with peripheral barbs which engage the wall of the left ventricle and the inter-ventricular septum. A third embodiment utilizes a single umbrella covered with a biocompatible membrane and provided with peripheral barbs which engage the wall of the left ventricle and the inter-ventricular septum. In both of the umbrella embodiments an aspiration tube coupling and valve are provided. The aspiration tube coupling allows an aspiration tube to aspirate the blood which has been segregated from the remaining portion of the ventricle and the valve prevents blood from reentering when the aspiration tube is uncoupled.

The catheter sheath with which the device is delivered to the left ventricle includes conduit channels, ports and other means for deploying the device, stabilizing it, anchoring it, expanding it, and disengaging from it. A suitable catheter for practicing the invention is one of the type used to install heart pacing electrodes, e.g. the catheter disclosed in U.S. Pat. No. 5,571,161 which is hereby incorporated by reference herein in its entirety.

The invention thus provides a percutaneous, intra-cardiac implantation device that directly reduces the amount of volume load on the left ventricle. As less volume is received in the left ventricle, the intra-cavity pressure is decreased, thereby reducing wall stress on the myocardium, decreasing oxygen demand and improving pump function. It is the shape, volume and size of the cavity of the ventricle that determines wall stress and not the external shape of the heart. In several embodiments of the invention, the dimensions of the cavity of the ventricle are changed but not the external shape of the ventricle. In other embodiments, the dimensions of the cavity are initially changed and thereafter as ventricular remodeling occurs the external shape of the ventricle is also favorably altered.

Additional objects and advantages of the invention will become apparent to those skilled in the art upon reference to the detailed description taken in conjunction with the provided figures.

BRIEF DESCRIPTION OF THE DRAWINGS

FIG. 3 is a schematic longitudinal sectional view of a first embodiment of an implantable expandable device in a catheter;

FIG. 3A is a schematic longitudinal sectional view of the first embodiment of an implantable expandable device in a catheter illustrating a preferred locking mechanism between the inflation tube and the central stem;

FIG. 4 is a schematic longitudinal sectional view of the first embodiment being anchored to the wall of the ventricle;

FIG. 8A is a illustrates another embodiment similar to FIG. 8;

DETAILED DESCRIPTION OF THE PREFERRED EMBODIMENTS

Figure 1:
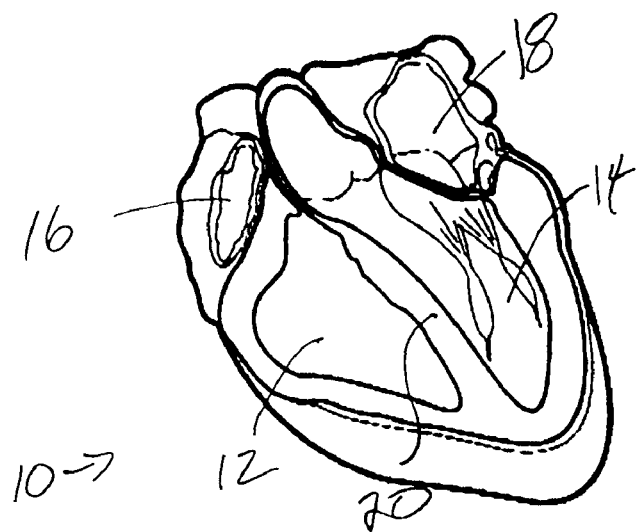
FIG. 1 is a schematic sectional view of a normal human heart.
Figure 2:
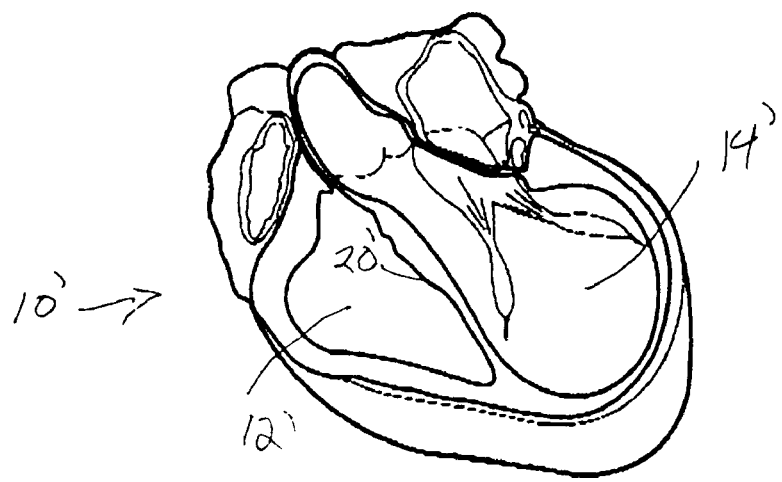
FIG. 2 is a schematic sectional view of a human heart afflicted with CHF.

Turning now to FIG. 3, an implantable expandable device 100 is shown inside a catheter sheath 102 and coupled to an inflation tube 104. The device 100 includes a central shaft 106 having a distal anchor 108, an inflatable balloon 110 surrounding the shaft 106, and a proximal coupling 112 with a self-closing valve 114. The valve 114 is in fluid communication with inflation ports 116. In this embodiment, the coupling 112 is a snap fit to which the inflation tube 104 is removably coupled. Referring to FIG. 3A, the snap fit coupling 112 includes a male-female type connection. The distal end of the inflation tube 104 has a cable operating or similar control mechanism, whereby, in a resting state, two spring loaded, lateral expansions 117 of the distal end of 104 itself, are opened to engage within the proximal end of the lumen of the central shaft 106. To disengage, the control mechanism (a button, lever etc) at the proximal control end (operator end) of the inflation tube 104 is activated to pull on control wires 115, whereby, the two lateral expansions are pulled radially inward and the snap fit into the central shaft is released, thus separating the inflation tube 104 from the central shaft 106. Reengagement is accomplished by, similarly, compressing the lateral expansions first, aligning the inflation tube and the central shaft (via fluoroscopic/ultrasound guidance) and then allowing the lateral expansions 117 to deploy, thereby securing a fit between the two.

The methods of the invention include delivering the catheter sheath 102 with the device 100 and inflation tube catheter 104 therein to the interior of the left ventricle in a trans-atrial septal fashion via the femoral vein or jugular vein. Alternatively, the device may be delivered via the femoral or brachial artery in a retrograde fashion through the aorta. The inflation tube 104 is then advanced relative to the catheter sheath 102 until the anchor 108 extends beyond the end of the catheter sheath 102. When entering through the jugular vein, the approach is to the right atrium, then across the inter-atrial septum to the left atrium and through the mitral valve into the left ventricle. The anchor 108 is then deployed into or through the apex of the left ventricle or into the septum or through the septum into the right ventricle. FIG. 4 illustrates the anchor 108 piercing the apex of the left ventricle 14'. It will be appreciated that the anchor is important to prevent balloon migration during cardiac contractions which could otherwise result in blockage of the mitral and/or aortic valves.

In the closed (un-deployed) position, the anchor 108 resembles a dart, and is advanced into the wall of the apex or beyond the apex of the ventricle or into the other ventricular cavity across the inter-ventricular septum. Once the desired position of the anchor is confirmed (on x-ray fluoroscopy), the anchor is deployed thereby preventing removal. This anchor deployment mechanism is activated via a wire passing along the catheter to the anchor either through the central stem of the balloon or on the outside of the balloon (when the balloon is in a collapsed position). Upon twisting the central wire, a torquing motion at its tip activates the anchor device. If the need arises to retrieve the balloon at a later date, the anchor can be reconfigured into a narrow dart to permit removal by twisting/untwisting (e.g., clockwise-anti-clockwise) a mechanism at the junction of the anchor 108 and the central shaft 106 of the balloon.

Figure 5:
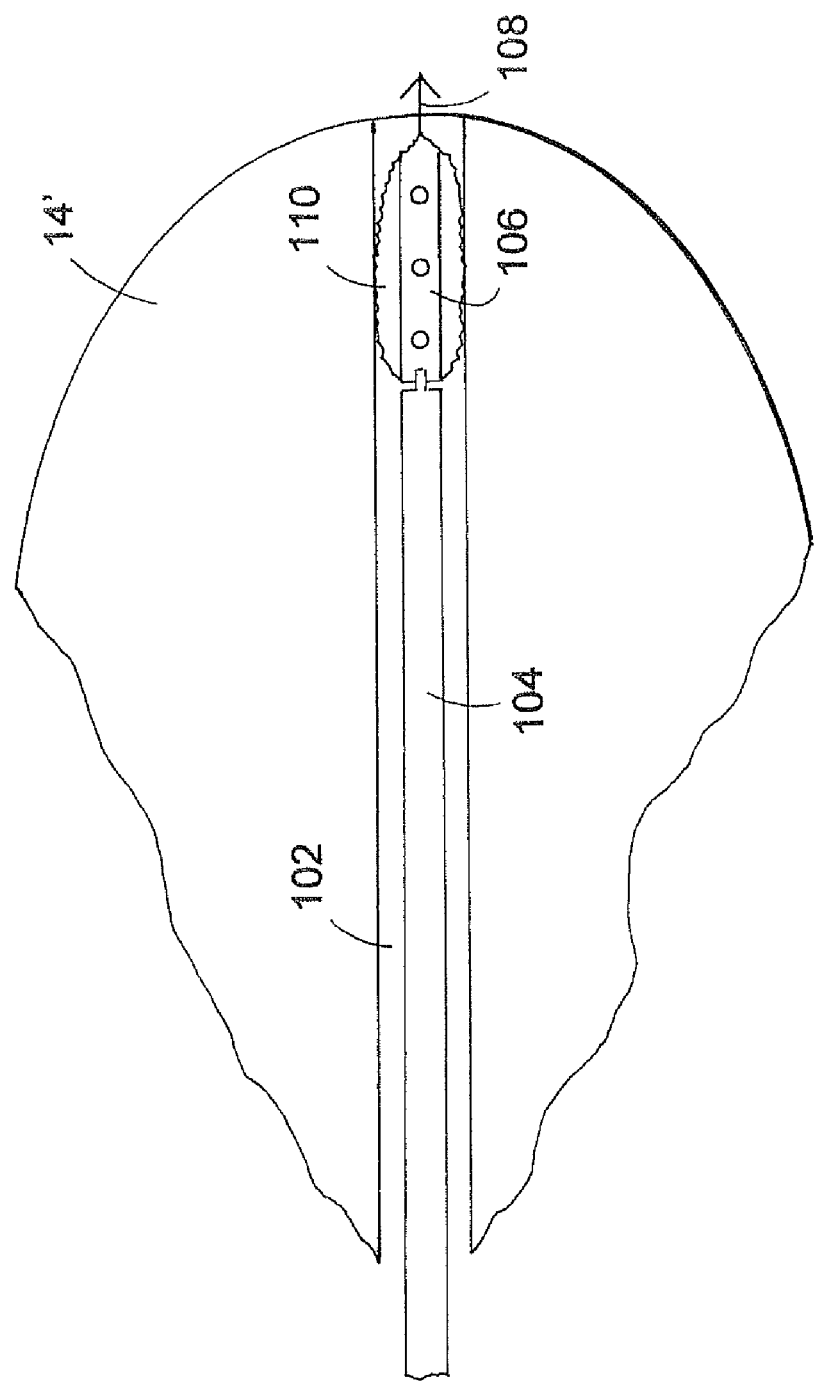
FIG. 5 is a schematic longitudinal sectional view of the first embodiment with the catheter partially withdrawn.
Figure 6:
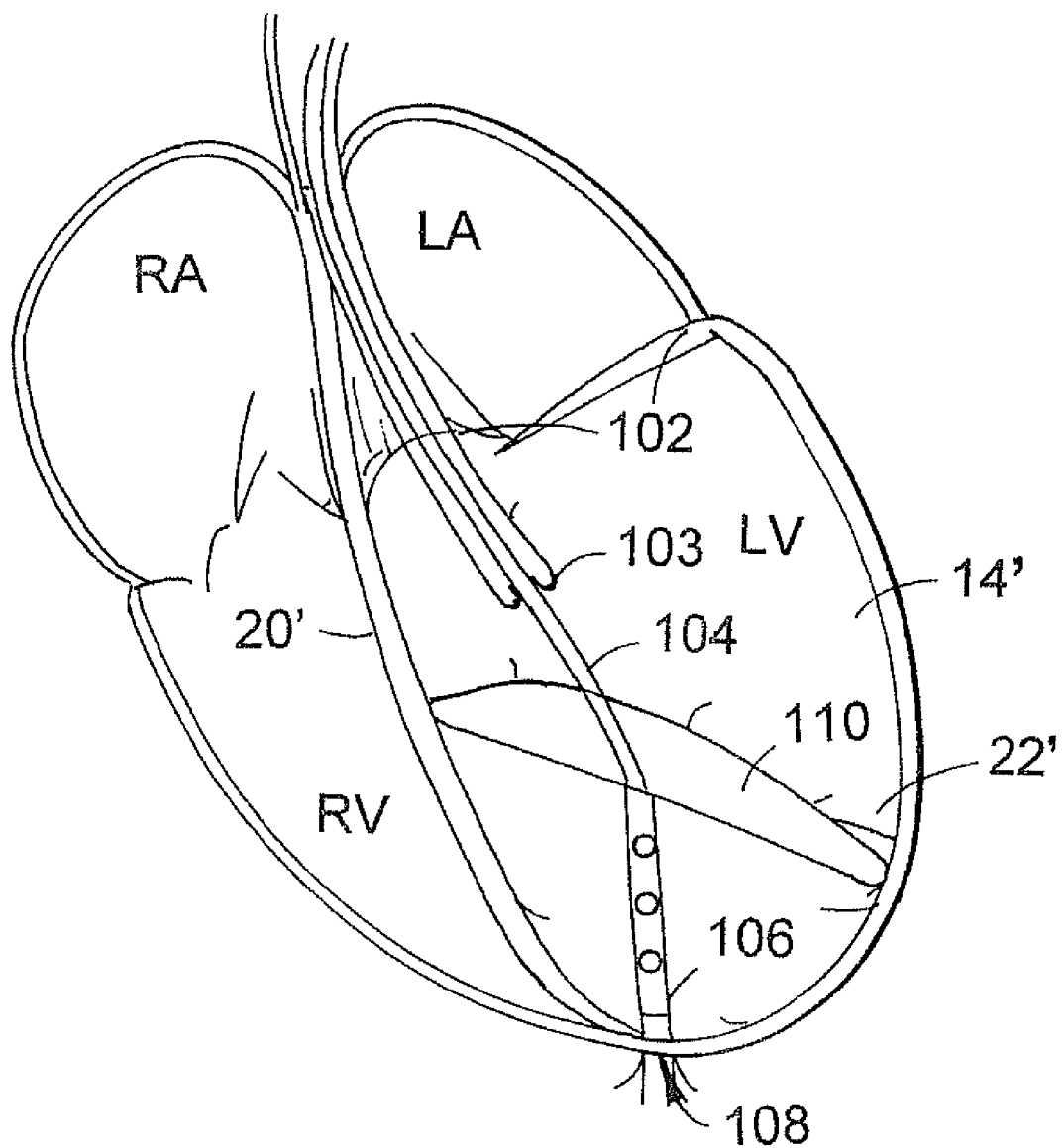
FIG. 6 is a schematic sectional view of the first embodiment anchored and inflated with the catheter partially withdrawn.

With the anchor 108 in place, the catheter sheath 102 is withdrawn exposing the inflatable balloon 110 as illustrated in FIG. 5. The balloon 110 is then inflated by injecting saline (or another biocompatible fluid preferably having a specific gravity equal to or less than that of blood) through the inflation tube 104 as shown in FIG. 6. It is important to note the preferred shape of the balloon 110. The shape is designed to reduce the size and also to restore the ellipsoidal shape of a healthy left ventricular cavity, and define a new ventricular apex 22'. The shape of the balloon can be described as "rotationally asymmetric about an axis". In the illustrated embodiment of FIG. 6 the axis can be considered the axis of the central shaft 106. More particularly, the shape is a paraboloid which is truncated at an angle relative to its directorix thereby producing the inclined upper surface shown in FIG. 6. As such, as shown in FIG. 6 the balloon also lacks line symmetry about a longitudinal center of the axis. The balloon is oriented so that the inclined upper surface preferably slopes down from the inter-ventricular septum as shown. With the high end of the upper surface positioned against the septum, there is no impedance to contraction by the middle and upper portions of the lateral wall of the left ventricle. In addition, pressure in the balloon should be sufficient to distend the balloon appropriately and yet keep the balloon compliant enough to avoid impeding the contraction of the myocardium.

As discussed above, the catheter 102 may be provided with a distal stabilizing configuration 103 which grips the inflation tube 104 to prevent lateral or other movement while engaging/disengaging from the balloon 110.

When the balloon 110 is expanded to the correct volume, the inflation tube 104 is decoupled from the coupling 112 (FIG. 3), as discussed above, and the self-closing valve 114 retains the saline inside the balloon. The inflation tube 104 and the catheter sheath 102 are then removed from the patient's body.

It will be appreciated that different size balloons 110 may be provided so that different size hearts may be treated. The expansion of the balloon can be monitored by fluoroscopy. Alternatively, each different size balloon can be indicated to contain a certain volume of saline when fully inflated. Inflation can then be monitored by metering the amount of saline which is injected into the balloon. It is presently preferred that pre-shaped balloons be provided in volumetric increments of 10 or 20 ml and that balloons range in size from 40 ml to 350 ml.

According to the preferred embodiments, the balloon 110 and anchor 108 are removable via the catheter 102 and inflation tube 104. The inflation tube is preferably re-attachable to the coupling 112 should the balloon ever need to be removed. When the inflation tube 104 is coupled to the coupling 112, the self-closing valve 114 opens and allows the saline to be suctioned, thus deflating the balloon.

The balloon is preferably soft, light weight, and compliant/compressible in order to prevent any interference with cardiac muscle contractions. It is also non-thrombogenic, inert (e.g. made from PTFE or suitable polyester) and impervious. It is capable of sustaining long-term implantation. It is preferably of unitary construction and capable of delivery via established catheter delivery systems. Radiopaque markers may be placed at strategic locations on the balloon and anchoring mechanisms to enable detection of the location and expansion of the balloon within the cavity during its insertion and future surveillance. Marker locations may be, for example, at the anchor, rim of the balloon, the self-closing valve, attachment/detachment location of balloon to catheter, central injection stem, etc.

Figure 7:
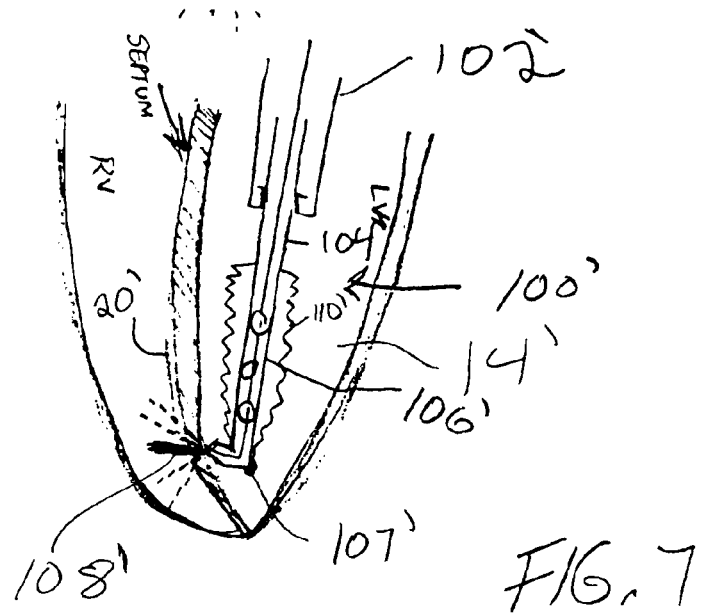
FIG. 7 illustrates an alternate embodiment with a hinged anchor for anchoring to the inter-ventricular septum.

Turning now to FIG. 7, an alternate embodiment 100' of the invention is similar to the embodiment 100 described above with similar reference numerals referring to similar parts. In this embodiment the central shaft has a distal hinge 107' which allows the anchor 108' to be rotated up to 90° so that it can be anchored to or through the septum 20' or other suitable areas of the apex of the ventricle. The hinge 107' is activated and controlled and fixed in position by control cables/channels or similar devices running the length of the inflation tube 104 and controlled by lever mechanisms at the operator end of the device. Anchoring is achieved by the central wire control system as described in the other embodiments. Sufficient lateral force is achieved by torquing of the inflation tube and if necessary by stabilizing the inflation tube within the catheter sheath 102 and thereby translating torquing force on 102 to the hinge 107. This is an established and standard industry method in widespread use, such as with steerable catheters and the trans-atrial septum catheters, when such lateral torquing motion is applied to pass through the inter atrial septum at right angles to the axis of catheter passage into the heart.

Figure 8:
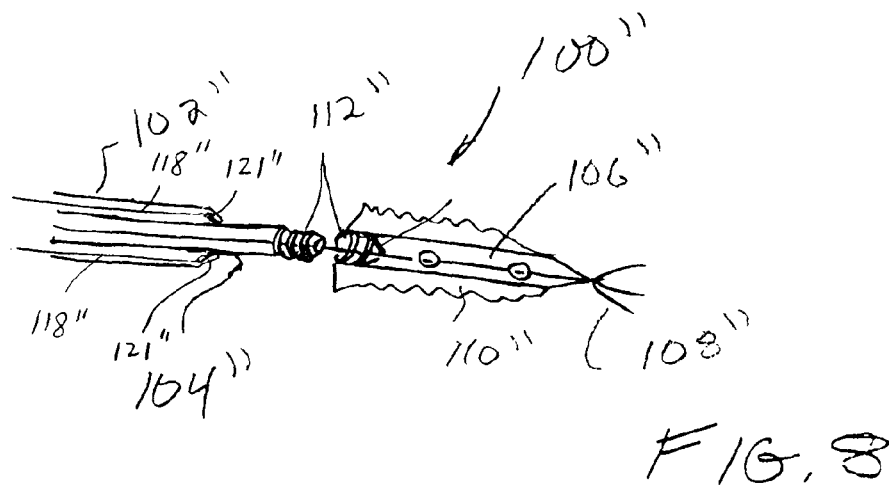
FIG. 8 illustrates an alternate embodiment with a threaded connector rather than a snap connector.

FIG. 8 shows yet another alternate embodiment 100" which is similar to the embodiment 100 described above with similar reference numerals referring to similar parts. The difference here is that the coupling 112" between the inflation tube 104" and the central shaft 106" is a rotational locking mechanism, such as a threaded coupling or a luer lock, with the inflation tube catheter 104 and central shaft 106 deployed in precoupled state. When adequate anchor to the apex and inflation of the balloon 110" is confirmed, the inflation tube and the central shaft are disengaged by a counter-clockwise torque motion of the inflation tube 104".

In order to facilitate torquing motion of the inflation tube 104", the distal end of the catheter sheath 102" may be also provided with a constricting mechanism which couples the catheter sheath and inflation tube catheter together for application of torquing motion to the inflation tube by the catheter sheath. For example, control wires 118" may be coupled to compressible elements such as leaves or pincers 121" at the distal end of the catheter sheath 102" producing a grasping/gripping effect, or a Teflon/PTFE cuff can be inflated at or purse-string coupled to the distal end of the catheter sheath. These mechanisms serve to stabilize the central shaft 106" or the distal end of the inflation tube catheter 104" for disengagement or reengagement as needed, and while the torquing motion is applied.

FIG. 8A shows a similar embodiment to FIG. 8, wherein the central shaft 106a" at its proximal alignment end to the inflation tube 104a" is preferably slightly longer than its balloon 110a" component so that enough purchase is afforded to the catheter sheath 102a" stabilizing mechanism to act upon.

Figure 9:
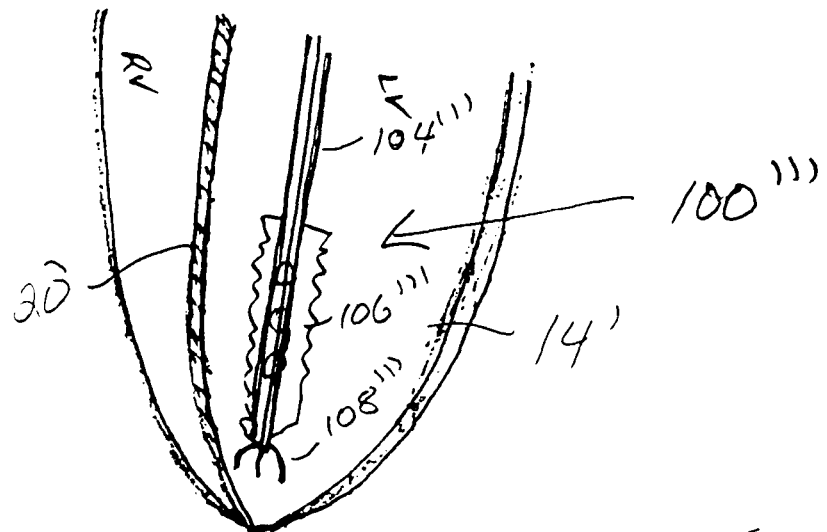
FIGS. 9 and 10 illustrate an alternate embodiment having a claw anchor.
Figure 10:
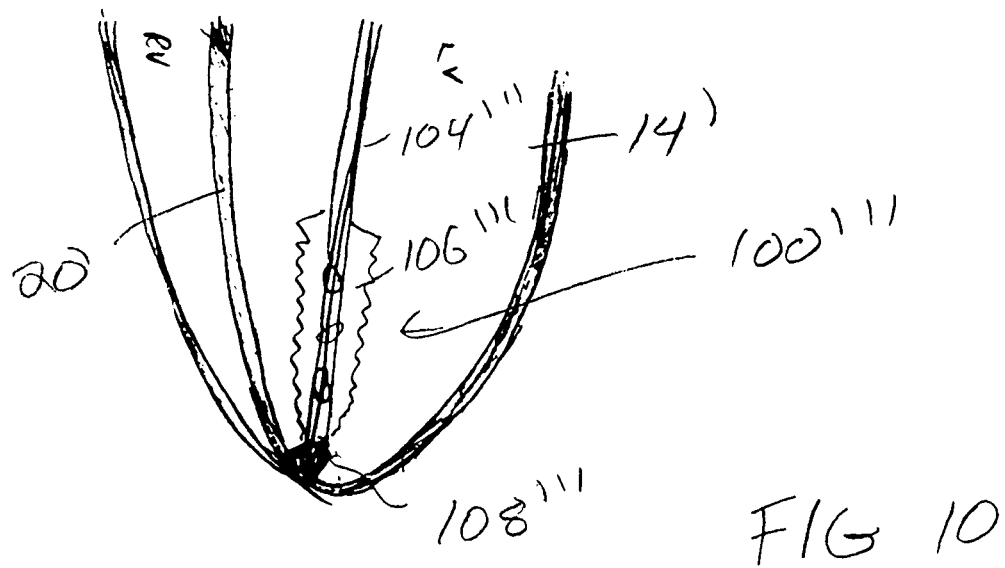

FIGS. 9 and 10 illustrate another alternate embodiment 100'" which is similar to the embodiment 100 described above with similar reference numerals referring to similar parts. The difference here is that the anchor 108''' is a group of claws. After the apparatus 100''' is delivered to the ventricle, the claws are opened as shown in FIG. 9. The claws are brought into engagement with the inside wall of the ventricle at the apex or the septum. After an adequate amount of myocardial tissue is grasped between the claws, they are closed as shown in FIG. 10.

More particularly, the anchor claws 108''' are aligned around the periphery of a cog wheel arrangement, the center of which has an opening for passage and insertion of the aligning end of the central wire passed through the inflation tube. The central wire is inserted into the lumen of the cog wheel arrangement and a torquing clockwise motion opens the cog wheel and the claws, and a counterclockwise motion closes it. After the desired effect, the central wire maybe withdrawn. Claws deployable into cardiac tissue and mechanisms for their deployment and release are well known to individuals skilled in the art of cardiac active pacing leads.

Figure 11:
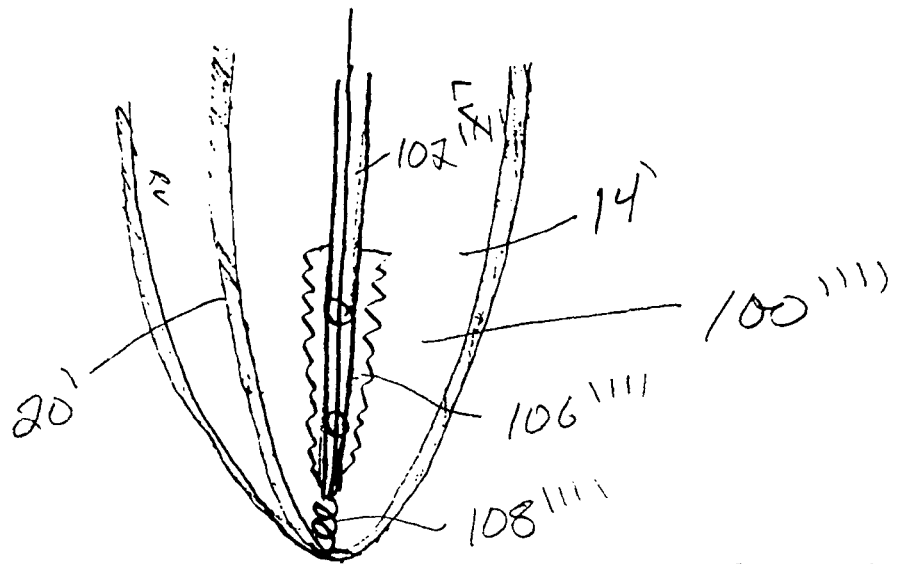
FIG. 11 illustrates an alternate embodiment having a cork screw anchor.

FIG. 11 illustrates another alternate embodiment 100'''' which is similar to the embodiment 100 described above with similar reference numerals referring to similar parts. The difference here is that the anchor 108'''' is a "cork screw" which is controlled by a wire passing through the central shaft 106''''. Alternatively, the cork screw may be threaded into the wall by a twisting motion of the whole catheter and central shaft without need for a central wire. Alternatively, the corkscrew may be threaded into the anchor site by stabilizing, fixing and immobilizing the distal end of the catheter sheath on the inflation tube and central shaft, thus making all three of these components into one single rigid torque tube.

Figure 12:
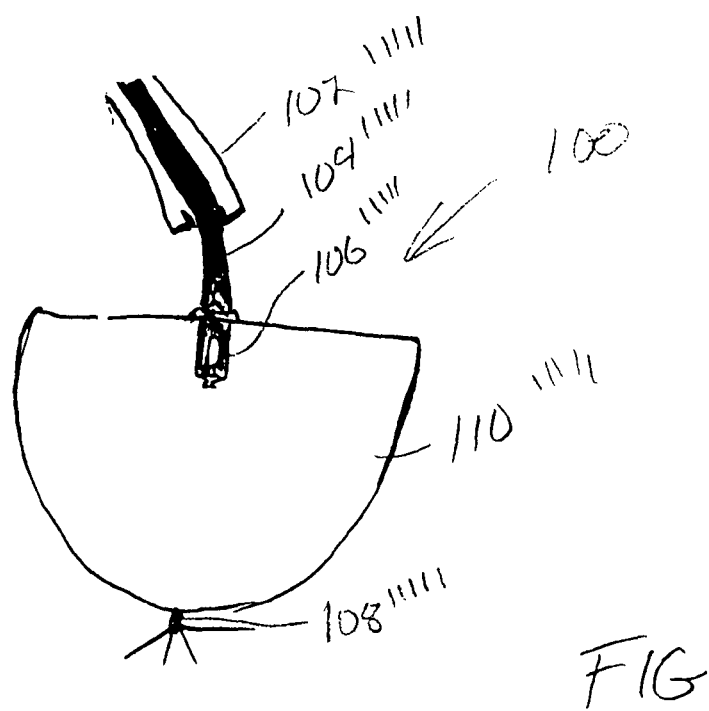
FIG. 12 illustrates an alternate embodiment having a short stem.

FIG. 12 illustrates another alternate embodiment 100''''' which is similar to the embodiment 100 described above with similar reference numerals referring to similar parts. The difference here is that the central shaft 106''''' is relatively shorter and does not extend through to the anchor 108''''' after the balloon 110''''' is inflated.

Figure 13:
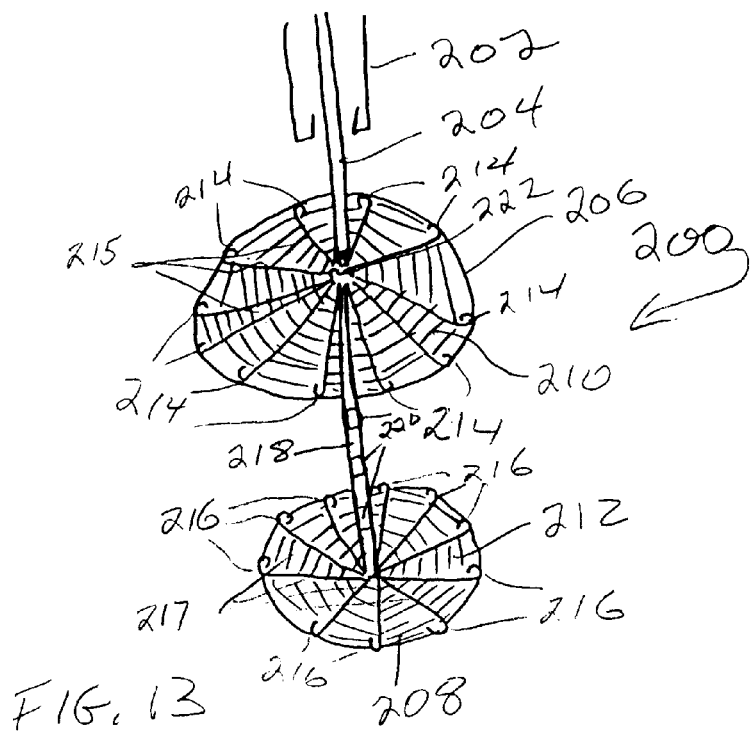
FIG. 13 is a schematic perspective view of a second embodiment of an implantable expandable device.
Figure 14:
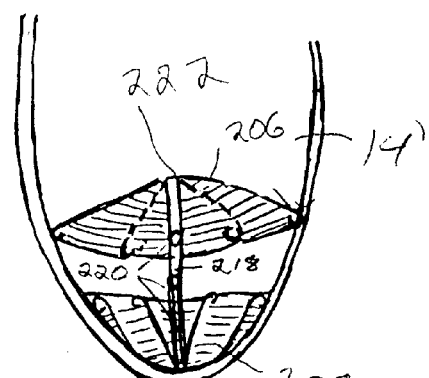
FIG. 14 is a schematic side elevation view of the second embodiment implanted in a ventricle.

Turning now to FIGS. 13 and 14, a second embodiment 200 of the device of the invention includes a catheter sheath 202 and a deployment/suction tube 204. In lieu of an inflatable balloon, this embodiment has two spaced apart biocompatible umbrellas 206, 208 which are each covered with a biocompatible membrane 210, 212. The periphery of each umbrella is provided with barbs 214, 216 which are located on the ends of radial spokes 215, 217, and the umbrellas are coupled to each other by a semi-rigid stem 218 which is provided with aspiration ports 220. The top of the stem 218 has a coupling 222 for removably coupling to the end of the tube 204. The coupling 222 includes a valve which automatically seals the passage into the stem 218 when the tube 204 is decoupled from it. Clock-wise or anti-clockwise rotation of the tube 204 (when coupled to the stem 218) produces an expanding or retracting motion on the radial spokes of the umbrellas. The articulating part of the catheter and the umbrella spoke attachments have a cog wheel configuration linkage that allows torque motion which opens or closes the umbrellas.

Figure 15:
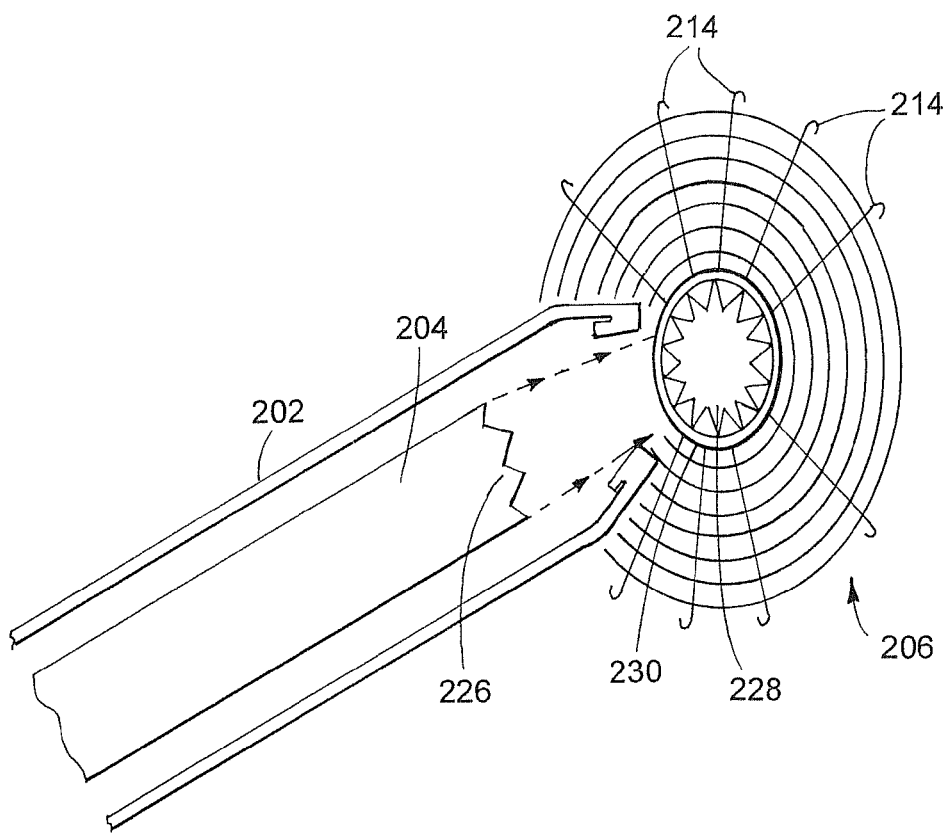
FIG. 15 is a schematic perspective view of the cog-wheel arrangement of the second embodiment of the invention.

More particularly, referring to FIGS. 13-15, the distal tip of the stem 218 (anchor end) and the distal tip of the tube 204 have circular cog wheel arrangements 226, which fit into complimenting recesses 228 in hubs 230 of the radial spokes of the distal and proximal umbrellas 206, 208. The device is pre-assembled in this fashion. Upon deployment of the anchor mechanism, the catheter sheath 202, tube 204, and the central shaft 218 are fixed by the stabilizing mechanism of the catheter sheath into a rigid component that torques the distal cog wheel 226 and the proximal cog wheel (not shown) such that it rotates clockwise the hub 228 of the radiating spokes, which expands the umbrellas 206, 208 and causes engagement of the barbs 214, 216 upon expansion to anchor the umbrellas. Now, the proximal end of the central shaft is disengaged from the inflation tube, and the stabilizing mechanism of the catheter sheath is deactivated, thus leaving the deployed umbrellas with their connecting central shaft in place inside the heart cavity. It will be appreciated from the figures that one umbrella is upside down and the other is right side up. The upside down umbrella 208 engages the apex of the ventricle and expands less and/or is smaller that the other umbrella 206.

The catheter, tube and umbrellas are delivered to the left ventricle with the umbrellas closed and inside the catheter. The umbrellas are pushed out of the catheter either by pulling back on the catheter while holding the tube or pushing forward on the tube while holding the catheter. The umbrellas are then opened until their barbs engage the ventricular wall and septum as shown in FIG. 4. Blood trapped between the umbrellas is aspirated via the ports and the tube. The vacuum used to aspirate also causes the umbrellas to further engage the ventricle wall and septum.

Figure 16:
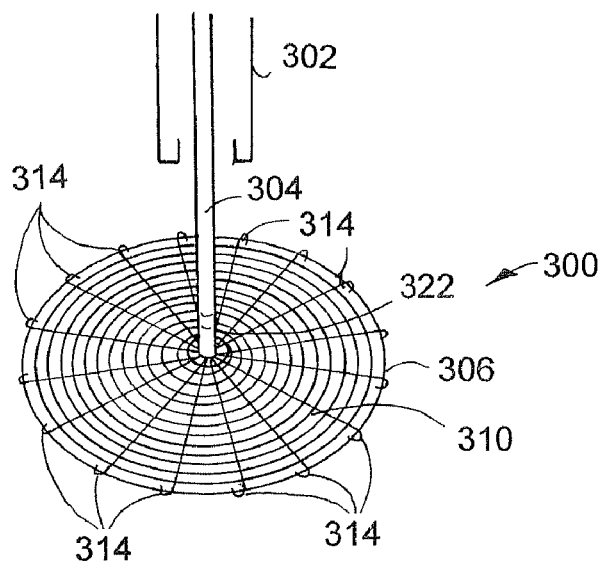
FIG. 16 is a schematic perspective view of a third embodiment of an implantable expandable device.
Figure 17:
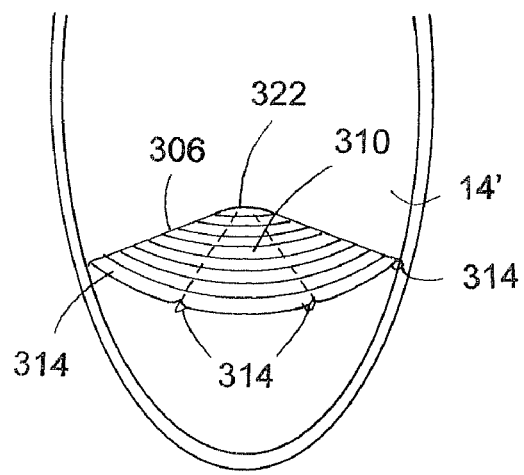
FIG. 17 is a schematic side elevation view of the third embodiment implanted in a ventricle.

FIGS. 16 and 17 illustrate a third embodiment 300 which is similar to the second embodiment just described. It includes a catheter 302, a deployment/aspiration tube 304, and an umbrella 306. The umbrella is covered with a biocompatible membrane 310. The periphery of the umbrella is provided with barbs 314 and the center of the umbrella is provided with a valved coupling 322. The valved coupling 322 allows the tube 304 to couple and uncouple from the umbrella. When the tube 322 is coupled to the umbrella, rotation of the tube causes the umbrella to open or close, as discussed above. After the umbrella is deployed, blood trapped between the apex of the ventricle and the umbrella is aspirated through the tube 304 and the tube is then uncoupled from the umbrella. At uncoupling, the valve 322 closes and prevents blood from reentering the space between the apex of the ventricle and the umbrella. Another alternate (non-illustrated) embodiment is similar to the embodiment 300 but includes a central stem extending from the center of the umbrella to the apex of the ventricle with an anchor at its tip.

Figure 18:
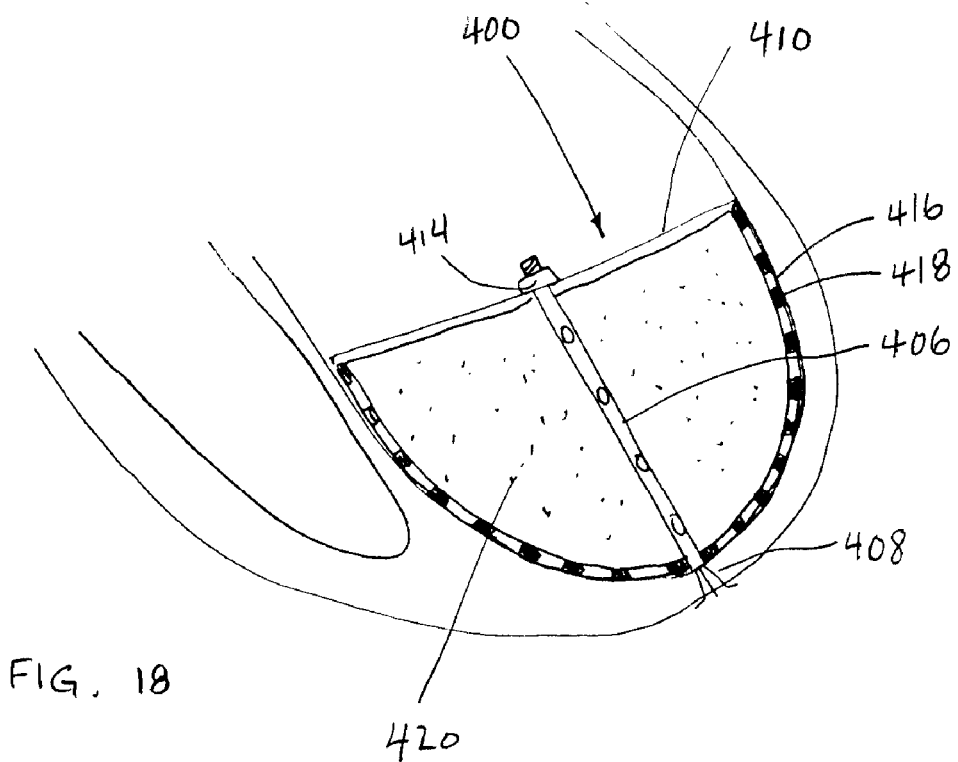
FIG. 18 is a schematic side elevation view of a fourth embodiment implanted in a ventricle.
Figure 19:
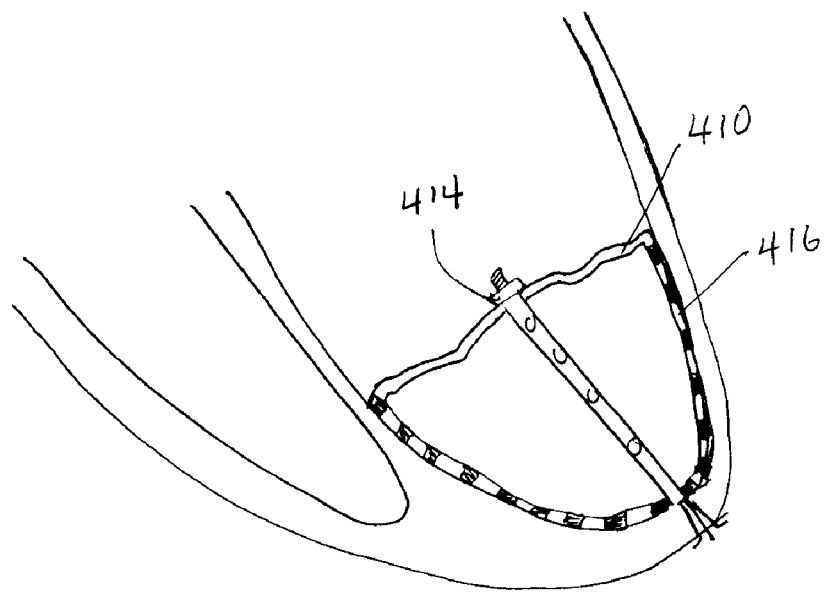
FIG. 19 is a schematic side elevation view of the fourth embodiment implanted in a ventricle and evacuated.

Turning now to FIG. 18, another embodiment of device for percutaneous ventricular restoration is shown. The device 400 includes a balloon 410 with a central perforate stem 406. The balloon 410 is coupled at the apex of the left ventricular substantially as described above, with an anchor 408. The sides of the balloon 410 include an abrasive and/or porous surface 416 preferably provided with an irritant coating 418, such as tetracycline or bleomycin or other such sclerosing agent. Such surface 416 and coating 418 enhances adhesion of the balloon 410 to the ventricular wall and promotes ingrowth of fibrous tissue from the ventricular wall onto the balloon. Inflation fluid 420 is delivered through a delivery tube (not shown) and valve 414 to expand the balloon within the apex of the ventricle so that the porous surface is in contact with the heart wall tissue. The expanded balloon, as shown in FIG. 18, is left in place for a period of time, e.g., eight to twelve weeks, to allow such ingrowth and tissue-to-balloon adhesion. Then, after the period of time required for tissue ingrowth, the patient undergoes a subsequent procedure during which the inflation fluid is percutaneously removed from the balloon by re-coupling a tube at the valve 414 and applying suction. Referring to FIG. 19, as the balloon 410 is evacuated and collapsed its volume is reduced, the diameter of the balloon decreases, thereby reshaping the ventricular cavity by causing movement of the left ventricular wall and the septum toward each other. Thus, not only the shape and size of the cavity of the ventricle is restored, but the external shape of the ventricle is also favorably altered. In an alternate embodiment, the top surface of the balloon may be thicker and non-compliant relative to the sides of the balloon, e.g., provided with stiffening ribs. Then, upon evacuation of the balloon, reshaping is limited to the sides of the balloon (rather than its top surface), maximizing movement of the lateral ventricular wall toward the septum.

Figure 20:
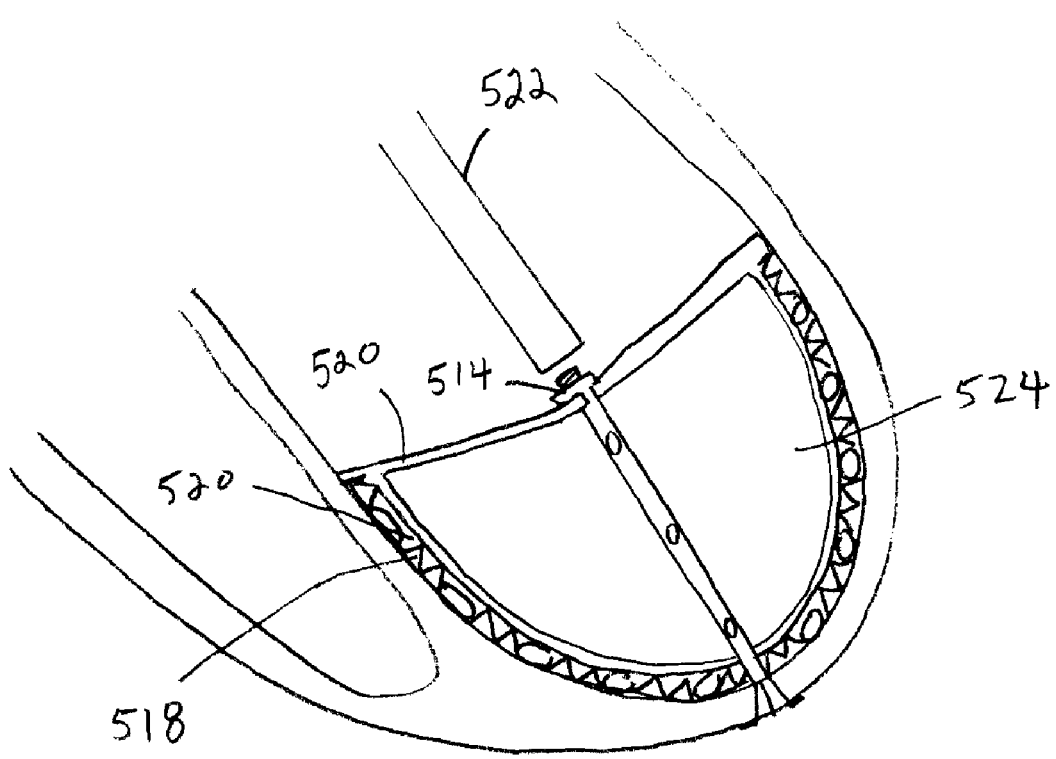
FIG. 20 is a schematic side elevation view of a fifth embodiment implanted in a ventricle.

Referring to FIG. 20, the wall 516 of the balloon 510 may be provided with a porous trabeculae or lattice 518 that forms a thin wall chamber 520 that is communicable with a suction source tube 522 applied at valve 514. By rotating suction source tube 522 relative to the valve 514 suction may be selectively applied to the interior of the balloon 524 or the chamber 520. Upon application of suction to the balloon wall chamber 520, the perforate outer surface of the balloon wall 516 adheres to the ventricular wall by way of negative pressure. The negative pressure can be maintained on the wall even after the active application of negative pressure is discontinued, creating adhesion similar to that created by a suction cup. In use, the balloon is inflated at the apex as described in prior embodiments to provide good balloon wall/tissue contact. Then, suction adhesion is created between the balloon wall and the ventricular wall. After suction adhesion is effected, the balloon may be evacuated of fluid by application of suction to the interior of the balloon. Such will reduce weight in the left ventricle in addition to reducing volume.

Figure 21:
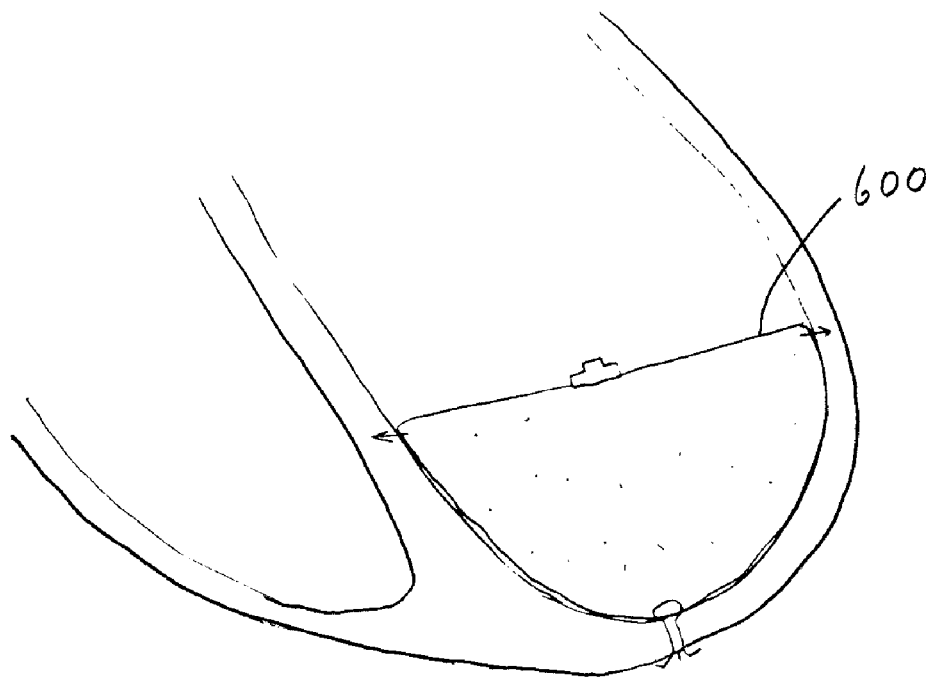
FIGS. 21 through 23 are schematic side elevation views of a sixth embodiment being implanted in a ventricle.
Figure 22:
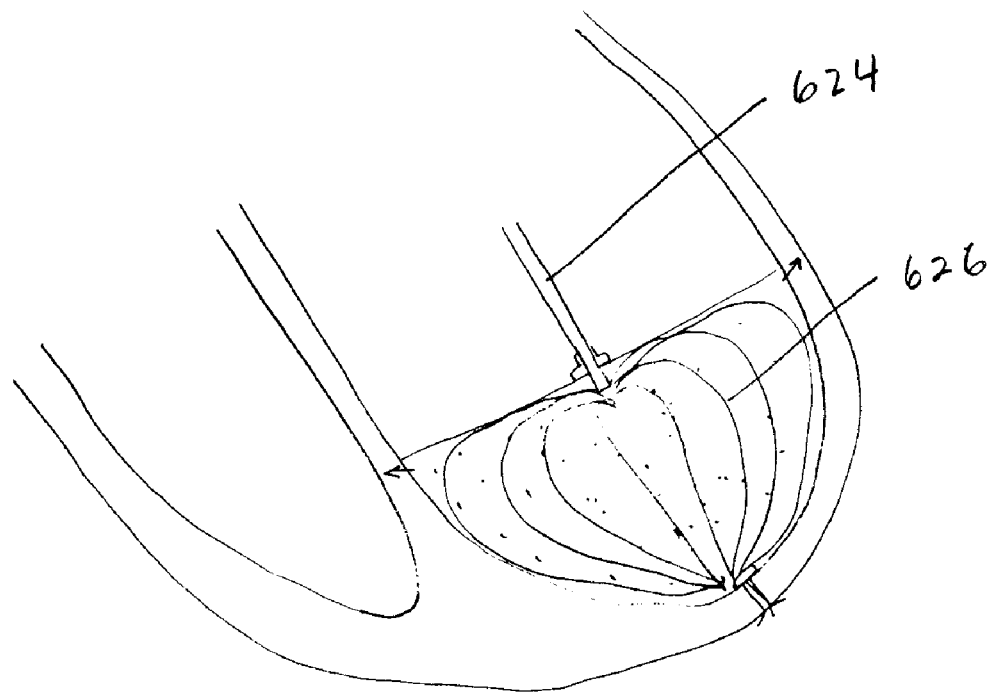
Figure 23:
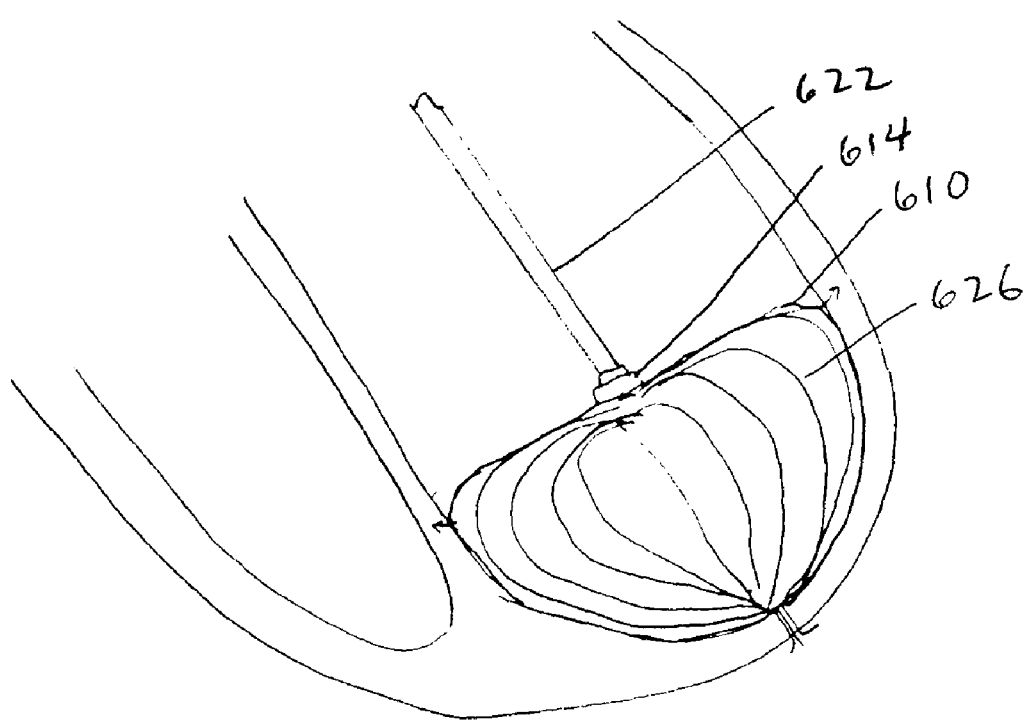

Turning now to FIGS. 21 to 23, another embodiment of a percutaneous device for modifying the volume of the left ventricle of the heart is shown. Referring to FIG. 21, the device is initially inserted as a balloon 610 anchored to the apex and about its upper surface, substantially as previously shown and described. The balloon is preferably, but not necessarily, inflated. Referring to FIG. 22, then through valve 614, a delivery device 624 provided with a collapsed basket 626 at its distal end is inserted into the interior of the balloon 610. The basket 626 is preferably spring-loaded to self expand to the interior periphery of the balloon upon retraction of a covering sheath (not shown). After basket insertion, the delivery device is then operated to retract the covering sheath to allow the basket to expand and decouple the basket into the interior of the balloon. Alternatively, the basket may be made from a shape memory alloy that can be activated to assume an expanded configuration upon application of heat or other energy, and the delivery device is then configured and operated to activate the basket to reconfigure from a collapse state into an expanded state once inserted into the balloon. Referring to FIG. 23, after expansion of the basket 626, if fluid is initially used to inflate the balloon 610, the fluid may be evacuated coupling a tube 622 to valve 614 and applying appropriate suction to the interior of the balloon.

Figure 24:
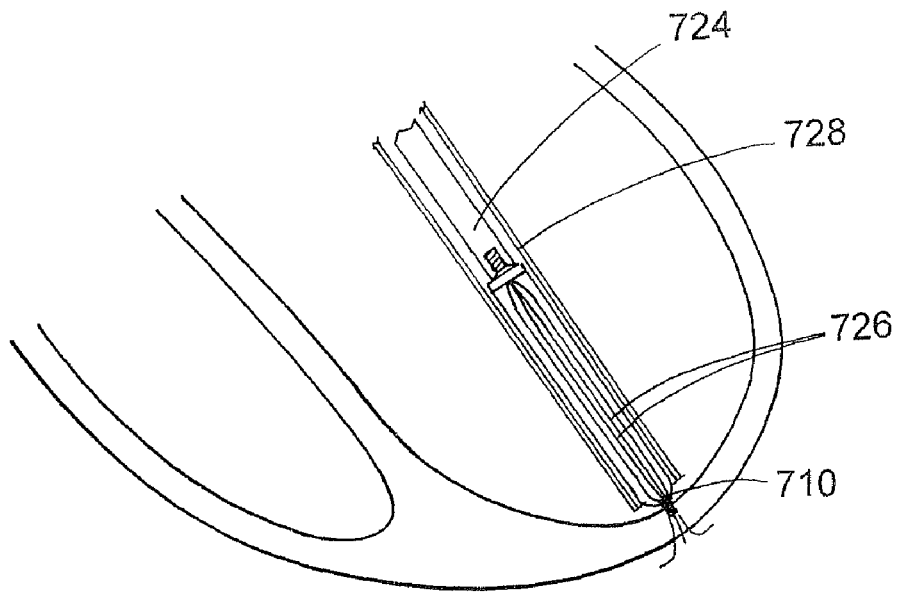
FIGS. 24 through 26 are schematic side elevation views of a seventh embodiment being implanted in a ventricle.
Figure 25:
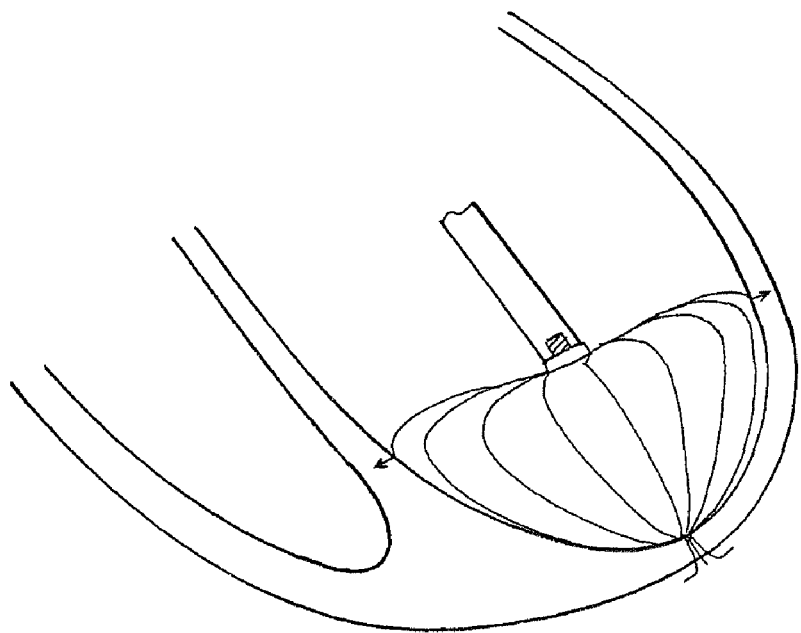
Figure 26:
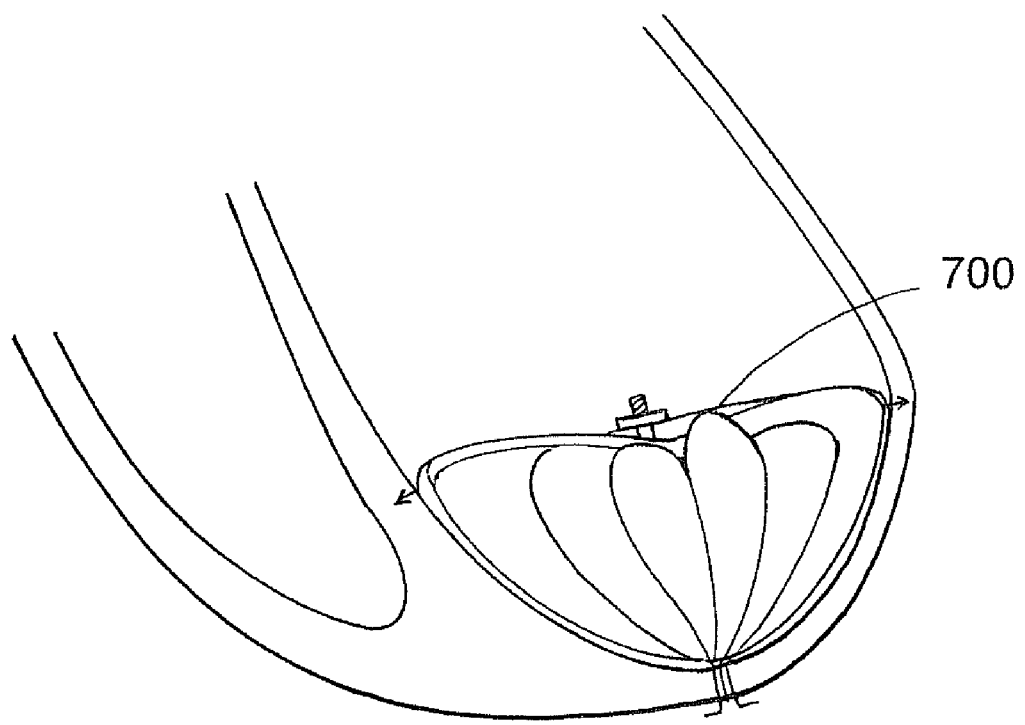

Turning now to FIGS. 24 to 26, another embodiment of a percutaneous device for modifying the volume of the left ventricle is shown. The device 700, provided at the distal end of a delivery instrument 724, is initially in the form of a radially collapsed wire basket 726 within a balloon 710. An outer sheath 728 confines the device 700 to the collapsed state (FIG. 24). The device 700 is delivered to the apex of the left ventricle and coupled thereat. Referring to FIG. 25, then the outer sheath 728 is retracted causing the device 700 to expand within the apex of the left ventricle. Finally, referring to FIG. 26, the delivery instrument 724 is decoupled from the device 700 and removed from the heart.

Figure 28:
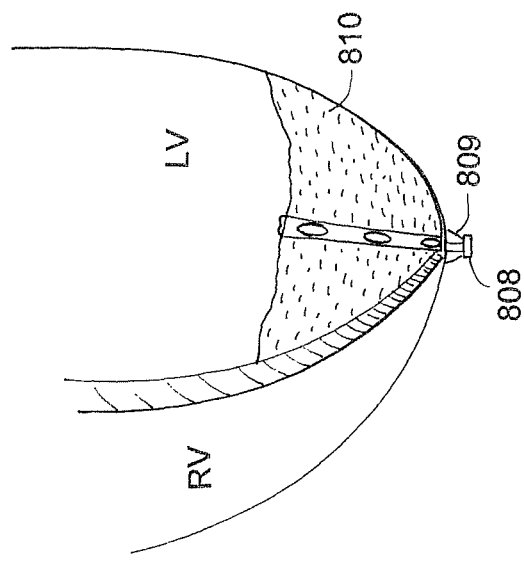
FIGS. 27 and 28 are schematic side elevation views of an eighth embodiment being implanted in a ventricle.
Figure 27:
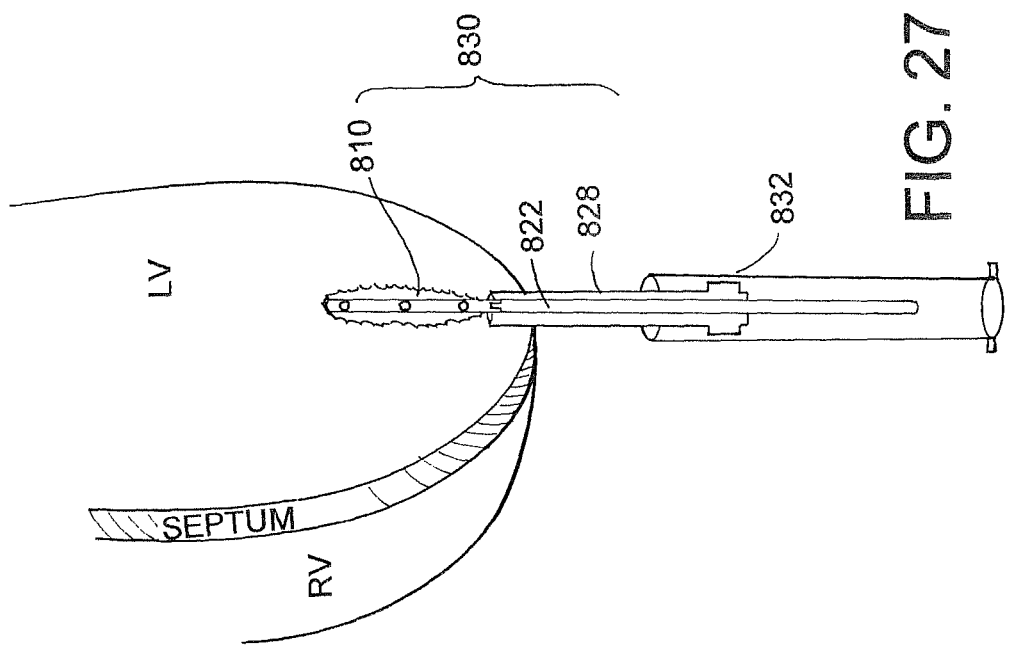

Turning now to FIGS. 27 and 28, the volume of the left ventricle may also be reduced in a non-percutaneous, but relatively minimally invasive approach via a sub-xiphoid incision or through a thoracoscope 832 via a left anterior thoracotomy incision. A delivery device 830 including an introducer 822, a balloon 810 preferably substantially similar to one of the embodiments described above at the distal end thereof, and a retractable sheath 828 over the balloon is advanced to the apex of the heart through the selected approach. The distal end of the delivery device 830 is inserted trans-apically into the left ventricle. The apical side of the balloon 810 includes an anchor 808 with an inflation valve 814. The balloon 810 is inflated through the inflation valve 814 and the anchor 808 is then pulled back through the apex of the heart wall. The anchor 808 is preferably locked to the wall with a button 809 or other suitable fastener. The anchor and button may be reliably coupled permitting removal of the balloon if necessary. A preferred attachment includes a releasable ratchet mechanism. The button 809 may be introduced over the introducer 822 and seated prior to releasing the introducer from the balloon 810, or the introducer may be released from the balloon and the button attached thereafter.

Figure 29:
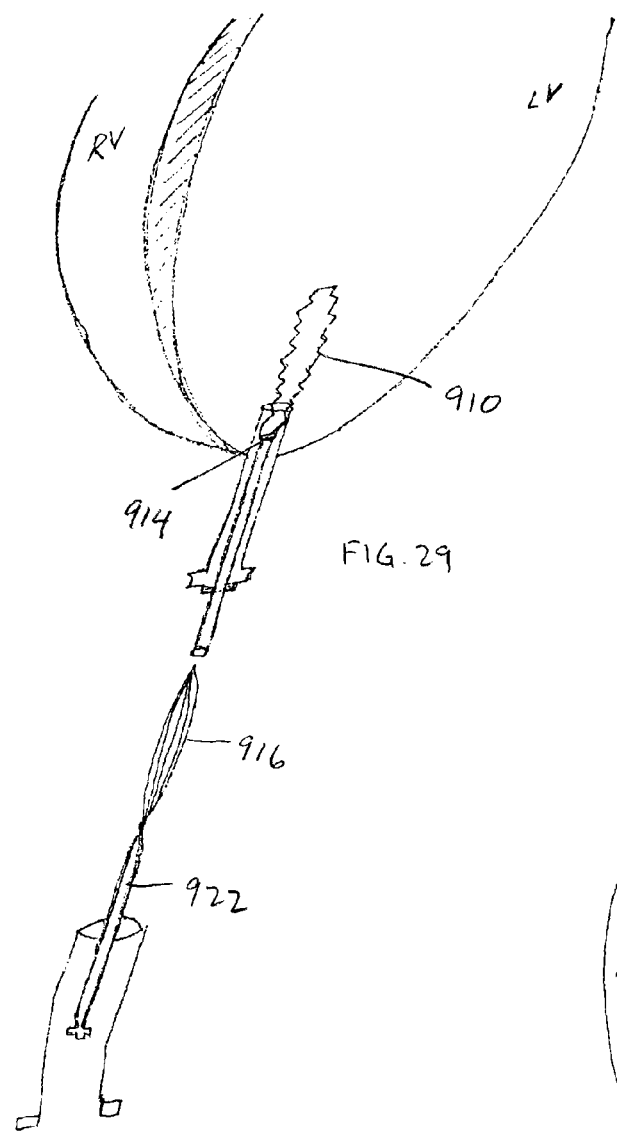
FIGS. 29 and 30 are schematic side elevation views of a ninth embodiment being implanted in a ventricle.
Figure 30:
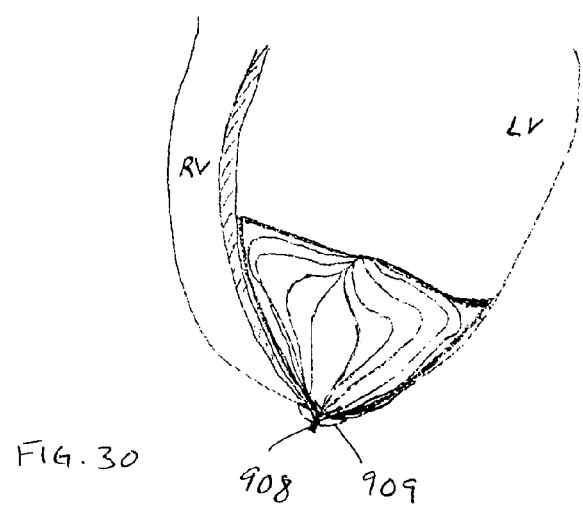

Referring to FIGS. 29 and 30, another minimally invasive embodiment is shown and now described. A balloon 910 is delivered trans-apically into the left ventricle. The balloon 910 has a valve 914 at its apical side. A collapsed basket 916 is introduced on a delivery device 922 into the balloon 910 and then expanded. The basket 916 may be self-expanding or comprised of a shape memory alloy expandable via application of appropriate energy. If energy is required, the delivery device 922 also includes an energy applicator to deliver the required energy for basket expansion. The apical end of at least one of the balloon and the basket includes an anchor 908, optionally for receiving a button 909, to couple the balloon/basket within the left ventricle. Such anchor 909 additionally comprises the site for energy reception to expand the basket, if necessary. Alternatively, the balloon 910 and basket 916 can be introduced together, as discussed above, into the left ventricle trans-apically.

There have been described and illustrated herein several embodiments of apparatus and a methods for ventricular restoration. While particular embodiments of the invention have been described, it is not intended that the invention be limited thereto, as it is intended that the invention be as broad in scope as the art will allow and that the specification be read likewise. Thus, while particular anchors have been disclosed, it will be appreciated that other anchors could be used as well. For example, a simple bayonet anchor could be used. In addition, while the presently preferred embodiment of the balloon has been described as a truncated paraboloid with the truncation plane at an angle to the directorix plane, other shapes could be used provided they yield equivalent results. For example, and not by way of limitation, the top surface of the balloon could be concave, convex, flat or angled. Other types of couplings between the inflation tube and the balloon could also be used, e.g. a bayonet coupling. Also, while the term balloon has been used, it is not necessary that the balloon be made of an elastic element, but such balloon should be made of a material relatively impermeable to the fluid (saline, blood) that must be kept in and/or out of the interior of the balloon for the given embodiment. It will therefore be appreciated by those skilled in the art that yet other modifications could be made to the provided invention without deviating from its scope as claimed.

What is claimed is:

1. An apparatus for percutaneous cardiac ventricular restoration, comprising:
    a balloon constructed in size and shape which permit said balloon to be delivered percutaneously to an interior of a ventricle in an unexpanded state, and expanded into an expanded state once said balloon has been delivered to the interior of the ventricle;

a basket integrated with said balloon, said basket adapted to apply an expansion force to said balloon to bias said balloon into said expanded state; and an anchoring device coupled to said balloon, said anchoring device adapted to anchor said balloon to a ventricular apex without coupling said balloon to a ventricular septum or a ventricular wall.

2. An apparatus according to claim 1, wherein:
said balloon includes a longitudinal axis, and said anchoring device is provided along said longitudinal axis.

3. An apparatus according to claim 1, further comprising:
a delivery device having structure which permits it to deliver said balloon in the unexpanded state percutaneously through a blood vessel to the interior of the ventricle.

4. An apparatus according to claim 3, wherein:
said delivery device includes a distal end, said basket is coupled to said distal end of said delivery device, and said delivery device is operable to expand said basket and release said basket from said distal end of said delivery device.

5. An apparatus according to claim 1, wherein:
said anchoring device is structured to penetrate at least partially through an apical wall of the heart.

6. An apparatus according to claim 1, wherein:
said anchoring device is structured to penetrate completely through an apical wall of the heart.

7. An apparatus according to claim 1, wherein:
said balloon is longitudinally asymmetrical when in the expanded state.

8. An apparatus according to claim 7, wherein:
said balloon is rotationally asymmetrical when in the expanded state.

9. An apparatus according to claim 1, wherein:
said balloon is rotationally asymmetrical when in the expanded state.

10. An apparatus according to claim 1, wherein:
said basket is self-expanding to the expanded state.

11. An apparatus according to claim 1, wherein:
said interior of said balloon is evacuated when said balloon is in said expanded state.

12. An apparatus for cardiac ventricular restoration of a heart having a ventricular septum, a ventricular wall and a ventricular apex therebetween, comprising:
a delivery device having an inflation lumen, a user-operated proximal end and a distal end;
a rotationally asymmetrical balloon releasably coupled to said distal end of said delivery device, said balloon constructed in a size and shape which permit said balloon to be delivered to an interior of the ventricle in an unexpanded state and being constructed to permit said balloon to be expanded once said balloon has been delivered to the interior of the ventricle;
said balloon having a valve and a coupling device, said coupling device for attachment relative to said inflation lumen for inflating said balloon, and said valve automatically closing to seal said balloon in a fluid-tight manner when said balloon is uncoupled from said distal end of said delivery device; and an anchoring device coupled to said balloon and having structure adapted to anchor said balloon to the ventricular apex, such that when said delivery device releases said balloon at the interior of the ventricle and said anchoring device is anchored to the ventricular apex, said balloon remains anchored within the ventricle with said valve sealing said balloon in the fluid-tight manner.

13. An apparatus according to claim 12, wherein:
said structure of said anchoring device anchors said balloon to the ventricular apex without anchoring said balloon to a ventricular septum or ventricular wall.

14. An apparatus according to claim 12, wherein:
said balloon in an unexpanded state is sized to be delivered percutaneously into the heart.

15. An apparatus for cardiac ventricular restoration of a heart having a ventricular septum, a ventricular wall and a ventricular apex therebetween, comprising:
an asymmetrical balloon constructed in a size and shape which permit said balloon to be delivered percutaneously to an interior of the ventricle in an unexpanded state and being constructed to permit said balloon to be expanded once said balloon has been delivered to the interior of the ventricle;
an expandable basket to expand the balloon after said balloon is in the interior of the ventricle;
a delivery device having a distal end to which said balloon is releasably coupled, said delivery device able to deliver said balloon in the unexpanded state percutaneously to the ventricular apex; and
an anchoring device coupled to said balloon and having structure adapted to anchor said balloon to the interior of the ventricle at the ventricular apex,
wherein once said balloon is anchored, said delivery device can be operated to release said balloon from said distal end of said delivery device.

16. An apparatus according to claim 15, wherein:
said structure of said anchoring device permits said balloon to be anchored at the ventricular apex without being anchored to the ventricular septum or the ventricular wall.

17. An apparatus for percutaneous cardiac ventricular restoration, comprising:
a balloon having an interior and constructed in size and shape which permit said balloon to be delivered percutaneously to an interior of a ventricle in an unexpanded state, and expanded into an expanded state once said balloon has been delivered to the interior of the ventricle, said balloon being evacuated of fluid at said interior of said balloon when in the expanded state; and
an anchoring device coupled to said balloon and having structure adapted to anchor said balloon to a ventricular apex without coupling said balloon to a ventricular septum or a ventricular wall.

18. An apparatus according to claim 17, further comprising:
a delivery device having structure which is adapted to deliver said balloon in said unexpanded state percutaneously through a blood vessel to the interior of the ventricle.

* * * * *